US012134791B2

(12) United States Patent
Becker et al.

(10) Patent No.: US 12,134,791 B2
(45) Date of Patent: Nov. 5, 2024

(54) ENZYME-CONTAINING, HOT-MELT GRANULES COMPRISING A THERMOTOLERANT DESICCANT

(71) Applicant: DANISCO US INC., Palo Alto, CA (US)

(72) Inventors: Nathaniel T. Becker, Burlingame, CA (US); Peyman Moslemy, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 689 days.

(21) Appl. No.: 16/956,262

(22) PCT Filed: Nov. 19, 2018

(86) PCT No.: PCT/US2018/061820

§ 371 (c)(1),
(2) Date: Jun. 19, 2020

(87) PCT Pub. No.: WO2019/125683

PCT Pub. Date: Jun. 27, 2019

(65) Prior Publication Data

US 2021/0222148 A1 Jul. 22, 2021

Related U.S. Application Data

(60) Provisional application No. 62/609,047, filed on Dec. 21, 2017, provisional application No. 62/628,057, filed on Feb. 8, 2018.

(51) Int. Cl.

| | |
|---|---|
| *C12N 9/16* | (2006.01) |
| *A23K 20/189* | (2016.01) |
| *A23K 20/28* | (2016.01) |
| *A23K 40/10* | (2016.01) |
| *A23L 29/00* | (2016.01) |
| *A23P 10/20* | (2016.01) |
| *C05F 11/08* | (2006.01) |
| *C05G 3/70* | (2020.01) |
| *C05G 5/12* | (2020.01) |
| *C11D 3/12* | (2006.01) |
| *C11D 3/37* | (2006.01) |
| *C11D 3/386* | (2006.01) |
| *C12N 9/96* | (2006.01) |
| *C12N 9/98* | (2006.01) |

(52) U.S. Cl.

CPC .............. *C12N 9/98* (2013.01); *A23K 20/189* (2016.05); *A23K 20/28* (2016.05); *A23K 40/10* (2016.05); *A23L 29/015* (2016.08); *A23L 29/06* (2016.08); *A23P 10/20* (2016.08); *C05F 11/08* (2013.01); *C05G 3/70* (2020.02); *C05G 5/12* (2020.02); *C11D 3/1246* (2013.01); *C11D 3/128* (2013.01); *C11D 3/3749* (2013.01); *C11D 3/38636* (2013.01); *C11D 3/38681* (2013.01); *C12N 9/16* (2013.01); *C12N 9/96* (2013.01); *A23V 2002/00* (2013.01)

(58) Field of Classification Search

CPC ... C11D 3/38672; C11D 3/1246; C11D 3/128; C11D 17/0039

USPC .......................................................... 435/187

See application file for complete search history.

(56) References Cited

PUBLICATIONS

Guimaraes et al. AAPS PharmSCITech., 2017, 18(4), pp. 1-9. (Year: 2017).*

* cited by examiner

*Primary Examiner* — Tekchand Saidha
*Assistant Examiner* — Mohammad Y Meah

(57) ABSTRACT

Described are compositions and methods relating to enzyme-containing, hot-melt-prepared granules produced from a starting material that contains an amount of water sufficient to denature the enzyme under hot-melt processing conditions. The resulting granules are particularly useful in consumer and industrial products, such as detergent, animal feed, food, personal care and agricultural compositions.

24 Claims, 1 Drawing Sheet

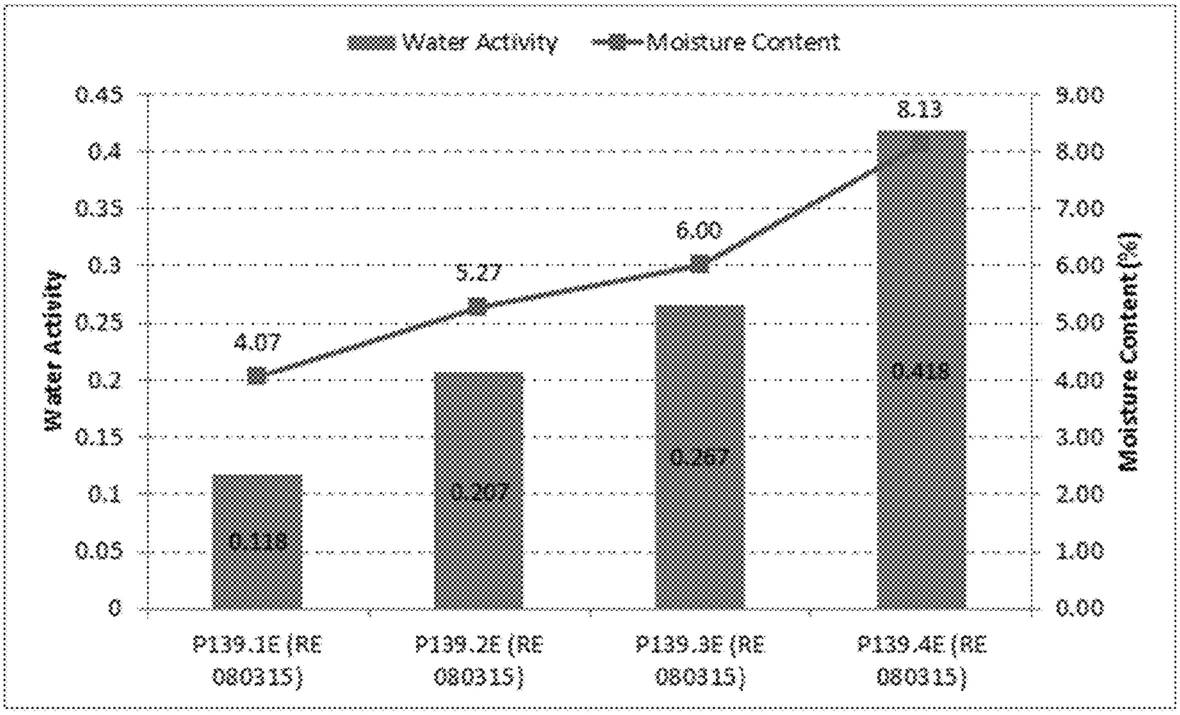
Water Activity
Moisture Content
0.45
0.4
0.35
0.3
0.25
0.2
0.15
0.1
0.05
0
Water Activity
9.00
8.00
7.00
6.00
5.00
4.00
3.00
2.00
1.00
0.00
Moisture Content (%)
4.07
5.27
6.00
8.13
0.118
0.207
0.267
0.418
P139.1E (RE 080315)
P139.2E (RE 080315)
P139.3E (RE 080315)
P139.4E (RE 080315)

ENZYME-CONTAINING, HOT-MELT GRANULES COMPRISING A THERMOTOLERANT DESICCANT

TECHNICAL FIELD

The present compositions and methods relate to enzyme-containing, hot-melt-prepared granules produced from a starting material that contains an amount of water that, if free, would be sufficient to denature an enzyme under hot-melt processing conditions. The granules are particularly useful in consumer and industrial products, such as detergent, animal feed, food, personal care and agricultural compositions.

BACKGROUND

The formulation of heat-sensitive bioactive agent compositions under stressful granulation conditions, particularly those encountered in hot-melt granulation conditions, is often complicated by substantial loss of bioactivity due to the presence of residual free or mobile water in active protein powders and or in inactive excipients employed in the granulation process. Most specific to the field of industrial enzymes and the present invention, is the granulation of enzyme compositions in hot-melt processes, such as hot-melt spinning disc atomization (also referred to as rotary disc or cup atomization), hot-melt extrusion, and spray cooling (also referred to as spray chilling, spray congealing, and prilling) at elevated temperatures. Spinning disc atomization of pharmacologically active agents is described in U.S. Pat. Nos. 7,261,529 and 7,758,778. Hot melt extrusion of pharmaceutical formulations is described in U.S. Pat. Nos. 9,192,578 and 9,730,894. Spray cooling of enzyme granules is described in U.S. Pat. No. 4,016,040.

The need exists for compositions and methods that allow the use of hot-melt granulation methods, particularly as they apply to relatively delicate enzymes.

SUMMARY

The present compositions and methods relate to enzyme-containing, hot-melt-prepared granules produced from a starting material that contains an amount of water that, if free, would be sufficient to denature an enzyme under hot-melt processing conditions. Aspects and embodiments of the compositions and methods are described in the following, independently-numbered paragraphs.

1. In one aspect, a hot-melt-prepared enzyme granule with low water activity is provided, comprising a mixture of a particulate enzyme powder and a desiccant that does not substantially release bound water at a temperature above 50° C.

2. In some embodiments of the granule of paragraph 1, the mixture of the particulate enzyme powder and the desiccant maintains a water activity of less than 0.15, optionally less than 0.10, optionally less than 0.08, optionally less than 0.05, optionally less than 0.01, and even optionally less than 0.005, for a preselected period of time.

3. In another aspect, a hot-melt-prepared enzyme granule with low water activity is provided, comprising a mixture of a particulate enzyme powder and a desiccant that maintains a water activity of less than 0.15, optionally less than 0.10, optionally less than 0.08, optionally less than 0.05, optionally less than 0.01, and even optionally less than 0.005, for a preselected period of time.

4. In another aspect, a hot-melt enzyme composition is provided, comprising a mixture of a particulate enzyme powder and a desiccant that maintains a water activity of less than 0.15, optionally less than 0.10, optionally less than 0.08, optionally less than 0.05, optionally less than 0.01, and even optionally less than 0.005 during melt granulation process, and optionally for a preselected post-granulation period of time.

5. In some embodiments of the granule of any of the preceding paragraphs, the desiccant does not substantially release bound water at a temperature less than 180° C.

6. In some embodiments of the granule of any of the preceding paragraphs, the ratio of enzyme powder to desiccant is between 0.1:10 (w/w) to 10:0.1 (w/w), optionally between 0.1:5 (w/w) to 5:0.1 (w/w) and optionally between 0.1:1 (w/w) to 1:0.1 (w/w).

7. In some embodiments of the granule of any of paragraphs 1-5, the ratio of enzyme powder to desiccant is between about 2:1 (w/w) to 4:1 (w/w).

8. In some embodiments of the granule of any of the preceding paragraphs, the desiccant is a zeolite.

9. In some embodiments of the granule of any of the preceding paragraphs, the desiccant is a zeolite having a $SiO_2/Al_2O_3$ ratio of less than 20.

10. In some embodiments of the granule of any of the preceding paragraphs, the desiccant is a zeolite with low-silica having a $SiO_2/Al_2O_3$ ratio of less than 4.

11. In some embodiments of the granule of any of the paragraphs 1-9, the desiccant is a zeolite with low-to-intermediate-silica having a $SiO_2/Al_2O_3$ ratio between 4 and 10.

12. In some embodiments of the granule of any of the paragraphs 1-9, the desiccant is a zeolite with intermediate-to-high-silica, having a $SiO_2/Al_2O_3$ ratio between 10 and 20.

13. In some embodiments of the granule of any of the preceding paragraphs, the desiccant is a zeolite with pores smaller than 1.0 nm, optionally smaller than 0.75 nm, optionally smaller than 0.60 nm, and optionally smaller than 0.40 nm.

14. In some embodiments of the granule of any of the preceding paragraphs, the desiccant is an activated zeolite, where it is dehydrated to at least 5% of its original water content, optionally at least 50% of its original water content, and optionally at least 95% of its original water content.

15. In some embodiments of the granule of any of the paragraphs 1-7, the desiccant is a diatomaceous earth (DE).

16. In some embodiments of the granule of paragraph 15, the desiccant is a diatomaceous earth (DE) with a water absorption capacity of at least 140 g water per 100 g of DE at room temperature, optionally at least 180 g water per 100 g of DE at room temperature, and optionally at least 200 g water per 100 g of DE at room temperature 17. In some embodiments of the granule of paragraphs 15 or 16, the desiccant has a water absorption capacity of at least 20 g water per 100 g of desiccant at 50° C.

18. In some embodiments the granule of any of the preceding paragraphs further comprises a colored saturation indicator.

19. In some embodiments of the granule of any of the preceding paragraphs, the preselected period of time is at least 5 minutes, at least 15 minutes, at least 1 hour, at least 12 hours, at least 24 hours, at least 48 hours, or more.

20. In another aspect, a detergent, animal feed, food, personal care or agricultural composition comprising the granule of any of paragraphs 1-19 is provided.

21. In another aspect a method for reducing the water-mediated degradation and/or deactivation of an enzyme in hot-melt-prepared granule comprising a particulate, enzyme-containing powder is provided, the method comprising adding to the enzyme powder prior to granulation a desiccant selected to not substantially release bound water at a temperature above 50° C. to produce a particulate enzyme mixture having, prior to granulation, a water activity of less than 0.3.

22. In some embodiments of the method of paragraph 21, the water activity of the particulate enzyme mixture prior to granulation is less than 0.15, optionally less than 0.10, optionally less than 0.08, optionally less than 0.05, optionally less than 0.01, and even optionally less than 0.005.

23. In some embodiments of the method of paragraph 21 or 22, the desiccant does not substantially release bound water at a temperature less than 180° C.

24. In some embodiments of the method of any of paragraphs 21-23, the desiccant is a zeolite.

25. In some embodiments of the method of any of paragraphs 21-23, the desiccant is a diatomaceous earth.

26. In some embodiments of the method of any of paragraphs 21-25, the features of any of paragraphs 1-20 are further incorporated.

These and other aspects and embodiments of present compositions and methods will be apparent from the description, including the accompanying FIGURE.

BRIEF DESCRIPTION OF THE DRAWINGS

FIG. 1 is a bar graph showing the water activity and residual moisture content of a phytase in granules produced using hot-melt spinning disc atomization.

DETAILED DESCRIPTION

I. Introduction

The present compositions and methods relate to stable, enzyme-containing, hot-melt granules comprising a thermotolerant desiccant. A desiccant is a hygroscopic substance that rapidly induces or sustains a state of dryness (i.e., desiccation) in its surrounding medium. The granules are prepared using particulate enzyme powders that have very low water activity ($a_w$) as a result of selecting a desiccant that binds free water in the starting material for the duration of the elevated-temperature processing of the granules; thereby, preventing enzyme degradation and/or deactivation that occurs in the presence of even minor amounts of free residual water under the stressed conditions of processing and handling at elevated temperatures.

While the use of desiccants in various applications is well known, desiccants, particularly thermotolerant desiccants, have not previously been added to particulate enzyme-containing powders. This is likely because spray drying is generally sufficient to produce a particulate enzyme powder having a water activity ($a_w$) of about 0.3, or less, which is sufficient to minimize water-mediated enzyme degradation or deactivation under typical enzyme storage and use conditions. However, the use of hot-melt granulation of enzymes imposes significant stresses on particulate enzyme formulations causing significant degradation and/or deactivation. It has surprisingly been discovered that such degradation and/or deactivation is not due to the elevated temperatures per se (i.e., the result of thermal protein denaturation) but rather due to the effect of elevated temperature on water-mediated degradation and/or deactivation resulting from minor amounts of free or mobile water that is present in enzyme powders or its surrounding environment.

It was therefore surprising to find the careful selection of a desiccant for combination with enzyme powder, can convert water present as free residual moisture to bound water even at elevated temperatures and, thereby, reduce or eliminate degradation and/or deactivation in what was previously believed to be at least primarily a thermal denaturation process, which denaturation process the skilled person would not think to prevent or ameliorate by the use of a desiccant, and would, accordingly, not provide impetus to the use of a desiccant as a solution to the problem.

II. Definitions and Abbreviations

Prior to describing embodiments of present compositions and methods, the following terms are defined.

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, the preferred methods and materials are described herein. Accordingly, the terms defined immediately below are more fully described by reference to the specification as a whole. Also, as used herein, the singular terms "a," "an," and "the" include the plural reference unless the context clearly indicates otherwise. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, a "particulate enzyme powder" is a substantially solid composition that includes an enzyme and up to about 6% water (w/w).

As used herein, a "desiccant-stabilized enzyme" includes a particulate enzyme powder admixed with a thermotolerant desiccant.

As used herein, a "desiccant" is a hygroscopic substance that binds water molecules so as to convert at least some free or mobile water to bound water wherein the bound water takes the form of chemically bound or physiosorbed water, or waters of crystallization.

As used herein a "thermotolerant desiccant" is a desiccant that binds water and does not substantially release the bound water" at a specified temperature of at least 50° C. The preferred "thermotolerant desiccant" releases less than 10% of its bound water at the specified temperature after 5 minutes at that temperature within the particular hot-melt composition.

As used herein, a desiccant "binds water" at a specified temperature if it releases less than 10% of bound water at the specified temperature after 5 minutes at that temperature within the particular hot-melt formulation.

As used herein, "room temperature" is 25° C.

As used herein, "elevated temperature" is a temperature of at least 50° C.

As used herein, the term “contacting,” means bringing into physical contact, such as by admixing dry chemicals, solutions, suspensions, and the like.

As used herein, a “solid” form of a chemical component refers to a powder, crystals, granules, agglomerates, aggregates, paste or wax thereof.

As used herein, a “liquid” form of a chemical component includes solutions, suspensions, slurries, and gels.

As used herein, the term “spray drying” refers to a method of producing a dry powder from a liquid or slurry by rapidly drying with a hot gas, as known in the art and discussed for example in U.S. Pat. No. 5,423,997 and WO 2008/088751A2.

As used herein, the term “UFC solids” refers to an ultrafiltrate concentrate produced from a fermenter/bioreactor, and is synonymous with enzyme concentrate solids. UFC solids may include both water-soluble and water-insoluble solids.

As used herein, “cleaning compositions” and “cleaning formulations” refer to compositions that may be used for the removal of undesired compounds from items to be cleaned, such as fabric, dishes, contact lenses, other solid substrates, hair (shampoos), skin (soaps and creams), teeth (mouthwashes, toothpastes) etc. The term encompasses any materials/compounds selected for the particular type of cleaning composition desired. The specific selection of cleaning composition materials are readily made by considering the surface, item or fabric to be cleaned, and the desired form of the composition for the cleaning conditions during use.

As used herein, the terms “detergent composition” and “detergent formulation” are used in reference to mixtures which are intended for use in a wash medium for the cleaning of soiled objects. In some preferred embodiments, the term is used in reference to laundering fabrics and/or garments (e.g., “laundry detergents”). In alternative embodiments, the term refers to other detergents, such as those used to clean dishes, cutlery, etc. (e.g., “dishwashing detergents”).

As used herein, “personal care products” means products used in the cleaning, bleaching and/or disinfecting of hair, skin, scalp, and teeth, including, but not limited to shampoos, body lotions, shower gels, topical moisturizers, toothpaste, and/or other topical cleansers. In some particularly preferred embodiments, these products are utilized on humans, while in other embodiments, these products find use with non-human animals (e.g., in veterinary applications).

A “suspension” or “dispersion” as used herein refers to a two-phase system wherein a discontinuous solid phase is dispersed within a continuous liquid phase. The solid phase can consist of very fine particles or larger granules, and the particles or granules can have a wide variety of shapes, morphologies and structures. For example, the solids can be spray-dried particles as small as 1 micron in diameter or larger core-shell granules between 100 and 1,000 microns in diameter.

The following abbreviations may be used in the description. Definitions are also provided as needed throughout the description.

| | |
|---|---|
| ° C. | degree Centigrade |
| Tm | melting temperature |
| $H_2O$ | water |
| $a_w$ | water activity |
| Min | minute |
| Hr | hour |
| w/w | weight/weight |

-continued

| | |
|---|---|
| wt % | weight percent |
| g or gm | grams |
| mM | millimolar |
| Mg | milligrams |
| Mg | micrograms |
| mL and ml | milliliters |
| μL and μl | microliters |

III. Enzyme-Containing, Hot-Melt Granules Comprising Desiccants

In general, spray dried enzyme powders produced using conventional spray drying have a water activity ($a_w$) of about 0.3, or less, corresponding to a moisture content of about 6%, or less. Such spray dried enzyme powders are often sufficiently stable under typical enzyme storage condition and yield a high amount of recovered/residual activity when used in final commercial applications. Such spray dried enzyme powders may also be sufficient for inclusion in many formulations, including granule formulations prepared by methods that require relatively low temperatures, e.g., less than about 50° C. A non-limiting example of such a method is fluid bed granulation.

For the purposes of hot-melt granulation, where temperatures exceed about 50° C., the present compositions and methods provide enzyme powders having an $a_w$ of no more than 0.3 or less, optionally no more than 0.2 or less, optionally no more than 0.15 or less, optionally no more than 0.10 or less, optionally no more than 0.08 or less, optionally no more than 0.05 or less, optionally no more than 0.01, and even optionally less than 0.005, or less, for a preselected period of time, as measured at room temperature. In some embodiments, the preselected period of time is at least 5 minutes, at least 15 minutes, at least 1 hour, at least 12 hours, at least 24 hours, at least 48 hours, or more (including weeks, months, years, or, essentially, indefinitely).

Such low water activity is achieved by the addition of a thermotolerant desiccant that is compatible with the ultimate commercial use of the enzyme-containing, hot-melt granule. Preferably, the thermotolerant desiccant is effective in reducing the $a_w$ of the enzyme powders relatively quickly to facilitate efficient product preparation, for example, within about 60 min, within about 45 min, within about 30 min, within about 15 min, or even within about 10 min following addition of the desiccant to the enzyme powder, i.e., contacting the enzyme powder with the desiccant. Furthermore the thermotolerant desiccant is capable of maintaining the low water activity at elevated temperatures of processing, handling or use, i.e., temperatures of at least 50° C.

In some embodiments, the ratio of enzyme powder to desiccant is between 0.1:10 (w/w) to 10:0.1 (w/w), between 0.1:5 (w/w) to 5:0.1 (w/w), or even between 0.1:1 (w/w) to 1:0.1 (w/w). In some embodiments, the ratio of enzyme powder to desiccant is about 2:1 (w/w) to about 4:1 (w/w).

A. Selection of Desiccants

An important feature of the compositions and methods is the selection of a thermotolerant desiccant that does not substantially release bound water at a temperature that is significantly higher than the temperatures encountered in processing, handling, storage or use, including the temperature or final commercial application temperature of the hot-melt-produced, enzyme-containing granules. Instead, the desiccant is selected to tightly bind water at the hot-melt temperatures used to prepare the granules, which are generally greater than about 50° C., in many cases, significantly greater. The thermotolerant desiccant may be described with respect to the temperature or range of temperatures at which it binds water, for example, a preferred desiccant should bind water at a temperature greater than 50° C., and/or in a temperature range of 500 to 180° C. Alternatively, or additionally, the thermotolerant desiccant is selected such that it does not substantially release bound water above about 50° C., below about 60° C., below about 70° C., below about 80° C., below about 90° C., below about 100° C., below about 110° C., below about 120° C., below about 130° C., below about 140° C., below about 150° C., below about 152° C., below about 160° C., below about 170° C., below about 180° C., or even higher.

The selection of a thermotolerant desiccant for a particular hot-melt application depends on the temperature expected to be encountered during the production of granules, the intended commercial end-use of the granules, environmental and toxicity requirement, and cost. Most generally, the thermotolerant desiccant should not release significant amounts of bound water above about 50° C., but in some cases the desiccant should be able to bind water without releasing it at even higher temperatures, e.g. above 50° C., 60° C., 70° C., 80° C., 90° C., 100° C., 110° C., 120° C., 130° C., 140° C., 150° C., 152° C., 160° C., 170° C., 180° C., and even above 180° C. Exemplary desiccants include activated alumina, aluminosilicates, aerogel, benzophenone, bentonite clay, calcium chloride, calcium oxide, calcium sulfate, cobalt chloride, copper sulfate, diatomaceous earth, lithium chloride, lithium bromide, magnesium sulfate, magnesium perchlorate, potassium carbonate, potassium hydroxide, silica gel, sodium, sodium chlorate, sodium chloride, sodium hydroxide, sodium sulfate, and sucrose.

A particular category of thermotolerant desiccants for use in the present compositions and methods are natural and synthetic zeolites. Extensive review of zeolites, their physical and chemical properties, and industrial application is provided in the Kirk-Othmer Encyclopedia of Chemical Technology (Cejka and Kubicka, 2010) and Ullmann's Encyclopedia of Industrial Chemistry (Broach et al., 2012).

Zeolites are generally described as crystalline, hydrated aluminosilicates with a three-dimensional framework structure constructed of $SiO_4$ and $AlO_4$ tetrahedra linked through oxygen bridges. The tetrahedra of $SiO_4$ and $AlO_4$ are the primary building blocks; the combination of which leads to the so-called secondary building units such as 4-, 5-, and 6-rings, double 4-, 5-, and 6-rings, and so on. Depending on the structure type, zeolites contain regular channels or interlinked voids whose aperture diameters are in the microporous range, i.e. below 2 nm. These pores contain water molecules and the cations necessary to balance the negative charge of the framework. The cations, which are mobile and can be exchanged, are mainly alkali metal or alkaline-earth metal ions.

The International Union of Pure and Applied Chemistry (IUPAC) provided guidelines for specifying the chemical formula for zeolites (see, e.g., McCusker, L. B. et al. (2003) "Nomenclature of structural and compositional characteristics of ordered microporous and mesoporous materials with inorganic hosts (IUPAC recommendations 2001)" *MicroporousMesoporousMater.* 58:3.). In the simplest form, a general formula can be given as:

$|M_{x/n}(H_2O)_y|[Al_xSi_{(t-x)}O_{2t}]$-LTA, wherein

- the guest species are listed between the braces, i.e., "||," and
- the host framework is listed between the brackets, i.e., "[ ],"
- M represents a charge-balancing cation such as Na, K, Ca or Mg,
- x is the number of framework Al atoms in the unit cell,
- n is the cation charge,
- y is the number of adsorbed water molecules,
- t is the total number of framework tetrahedral atoms in the unit cell (Al+Si), and
- LTA, herein entered as an example, is the code or the framework type.

In general, increasing framework Si/Al or $SiO_2/Al_2O_3$ composition changes the surface selectivity from hydrophilic to hydrophobic. A distinction can be made between low-silica ($SiO_2/Al_2O_3<4$), low-to-intermediate-silica ($4<SiO_2/Al_2O_3<10$), intermediate-to-high-silica ($10<SiO_2/Al_2O_3<20$) and high-silica ($20<SiO_2/Al_2O_3<200$) zeolites.

The preferred zeolites of the present compositions with respect to the $SiO_2/Al_2O_3$ ratio are Erionite ($SiO_2/Al_2O_3$ 2.1-3.8), Zeolite A ($SiO_2/Al_2O_3$ 2.0-6.8), Zeolite P ($SiO_2/Al_2O_3$ 2.0-5.0), Zeolite X ($SiO_2/Al_2O_3$ 2.0-3.0), Zeolite Y ($SiO_2/Al_2O_3$ 3.0-6.0), and Mordenite ($SiO_2/Al_2O_3$ 9.0-20). These zeolites are used as desiccant in closed or open systems, i.e., for the static or dynamic adsorption of water.

The presence of aluminum in the aluminosilicate framework introduces a negative charge of the framework. Organic or inorganic cations or protons located in the inner volume of zeolites compensate this negative charge. In addition, water molecules are present in zeolite channels, mainly coordinated by cations or protons. A straightforward relationship exists between the size and shape of zeolite entrance windows to the channel system and the kinetic diameter of water molecules (0.26 nm), having important consequences for application of zeolites in desiccation. In general, zeolites with even-rings are divided into the following four categories: (1) Small-pore zeolites (8-rings with pore dimensions up to 0.40 nm) like Erionite, Zeolite A and Zeolite P; (2) Medium-pore zeolites (10-rings with pore sizes up to 0.50-0.60 nm) like Zeolite ZSM-5 and ZSM-22; (3) Large-pore zeolites (12-rings up to 0.75 nm) like Mordenite, Zeolite L, Zeolite X and Zeolite Y; and (4) Extra-large-pore zeolites (at least 14-rings with pore sizes around 1.0 nm) like Zeolite CIT-5, UTD-1 and ECR-34.

The preferred zeolites of the present invention with respect to pore dimensions are Zeolite A (0.41 nm×0.41 nm), Zeolite P (0.31 nm×0.45 nm), Zeolite X (0.74 nm), Zeolite Y (0.74 nm), and Mordenite (0.65×0.70 nm).

In a preferred embodiment, the zeolites of the present compositions are dehydrated, or "activated", at least partially, to enhance their water adsorption capacity as desiccant in closed or open systems, i.e., for the static or dynamic adsorption of water. Exemplary types of dehydrated zeolites include Zeolite A and Zeolite X.

In one embodiment, the zeolites of the present compositions are dehydrated by at least 5%, at least 15%, at least 25%, at least 35%, at least 45%, at least 55%, at least 65%, at least 75%, at least 85%, or at least 95% from their original water content.

In one embodiment, the zeolites of the present compositions are not dehydrated, and are used as in their native state.

Another preferred particular category of porous desiccants for use in the present compositions and methods is the diatomaceous earth or diatomite.

Diatomaceous earth (DE) is a naturally occurring mineral composition of biogenic origin. It is the microscopic skeletal diatom remains of unicellular plants, deposited on the earth lakebeds and ocean floors over eons. The DE is intricately structured, highly absorptive, and chemically inert composed on nearly pure silica. It is thermally processed to make a broad range of powdered and granulated absorbents and functional additives. The DE has a characteristic complex natural morphology with typical low bulk density of 100-430 g/L, porosity of 85%, and high surface area (BET) of 15-70 $m^2$/gram.

The DE additives of interest for use in the compositions of the present invention have a water absorption capacity of at least 140 kg/100 kg DE. Exemplary DE additives include those marketed by EP MINERALS™ (Reno, Nevada, USA) under the trade name CELATOM®, including CELATOM® MN-2, MN-4, MN-23, MN-47, MN-51, MN-53, MN-84, MP-77, MP-78, MP-79, and MP-94.

The preferred DE additives of the present compositions have a water absorption capacity of at least 180 kg/100 kg DE such as CELATOM® MN-2 (200 kg/100 kg) and CELATOM® MN-4 (180 kg/100 kg).

It is known by the person skilled in the art that there are several adsorption mechanisms by which zeolites, diatomaceous earth and other desiccants can be used in practice. These mechanisms depend on the chemical and physical framework (e.g., Si/Al ratio in zeolites), pore size distribution, exchanged cations, and water content.

Clearly, not all the foregoing desiccants will satisfy the all the criteria of a particular application, but it should at a minimum be sufficiently thermotolerant so as not to release more than 10% of bound water at temperatures of at least 50° C. Beyond this minimum requirement, the skilled person can select an appropriate desiccant based on the particular needs of the compositions and methods, the present teachings, and general knowledge in the art.

B. Enzyme-Containing Protein Powders

The present compositions and methods are relevant to non-aqueous protein powders that include at least 1%, at least 2%, at least 3%, at least 4%, at least 5%, or even at least 6% water. The protein powder may be spray dried or otherwise processed. In some embodiments, the protein powder is the partially dried cell mass from a fermenter in which microbial cell producing commercially-relevant enzymes are grown. Such microbes are typically bacterial or fungal but may also be mammalian or plant. In some embodiments, the protein powder is prepared from ultrafiltered concentrate (UFC) or precipitate or of bulk cell mass. In other embodiments, the protein powder is prepared from purified or partially purified protein.

C. Enzymes that Benefit from the Use of Desiccants

The present compositions and methods are applicable to many different enzymes. Exemplary enzymes include acyl transferases, α-amylases, β-amylases, arabinosidases, aryl esterases, carrageenases, catalases, cellobiohydrolases, cellulases, chondroitinases, cutinases, endo-β-1,4-glucanases, endo-beta-mannanases, esterases, exo-mannanases, galactanases, α-galactosidases, β-galactosidases, β-glucanases, glucoamylases, hemicellulases, hyaluronidases, keratinases, laccases, lactases, ligninases, lipases, lipoxygenases, mannanases, oxidases, oxidoreductases, pectate lyases, pectin acetyl esterases, pectinases, pentosanases, perhydrolases, peroxidases, peroxygenases, phenoloxidases, phosphatases, phospholipases, phytases, polygalacturonases, proteases, pullulanases, reductases, rhamnogalacturonases, tannases, transglutaminases, xylan acetyl-esterases, xylanases, xyloglucanases, xylosidases, metalloproteases, additional serine proteases, and combinations, thereof.

Examples of proteases include but are not limited to subtilisins, such as those derived from *Bacillus* (e.g., subtilisin, lentus, amyloliquefaciens, subtilisin Carlsberg, subtilisin 309, subtilisin 147 and subtilisin 168), including variants as described in, e.g., U.S. Pat. Nos. RE 34,606, 5,955,340, 5,700,676, 6,312,936, and 6,482,628, all of which are incorporated herein by reference. Additional proteases include trypsin (e.g., of porcine or bovine origin) and the *Fusarium* protease described in WO 89/06270. In some embodiments the protease is one or more of MAXATASE®, MAXACAL™, MAXAPEM™, OPTICLEAN®, OPTIMASE®, PROPERASE®, PURAFECT®, PURAFECT® OXP, PURAMAX™, EXCELLASE™, and PURAFAST™ (DuPont Industrial Biosciences); ALCALASE®, SAVINASE®, PRIMASE®, DURAZYM™, POLARZYME®, OVOZYME®, KANNASE®, LIQUANASE®, NEUTRASE®, RELASE® and ESPERASE® (Novozymes); BLAP™ and BLAP™ variants (Henkel Kommanditgesellschaft auf Aktien, Duesseldorf, Germany), and KAP (*B. alkalophilus* subtilisin; Kao Corp., Tokyo, Japan). Additional proteases are described in WO95/23221, WO 92/21760, WO 09/149200, WO 09/149144, WO 09/149145, WO 11/072099, WO 10/056640, WO 10/056653, WO 11/140364, WO 12/151534, U.S. Pat. Publ. No. 2008/0090747, and U.S. Pat. Nos. 5,801,039, 5,340,735, 5,500,364, 5,855,625, US RE 34,606, 5,955,340, 5,700,676, 6,312,936, and 6,482,628.

Proteases include neutral metalloproteases including those described in WO 07/044993 and WO 09/058661. Other exemplary metalloproteases include nprE, the recombinant form of neutral metalloprotease expressed in *Bacillus subtilis* (see e.g., WO 07/044993), and PMN, the purified neutral metalloprotease from *Bacillus amyloliquefaciens.*

Lipases include, but are not limited to *Humicola lanuginosa* lipase (see e.g., EP 258 068, and EP 305 216), *Rhizomucor miehei* lipase (See e.g., EP 238 023), *Candida* lipase, such as *C. antarctica* lipase (e.g., the *C. antarctica* lipase A or B; See e.g., EP 214 761), *Pseudomonas* lipases such as *P. alcaligenes* lipase and *P. pseudoalcaligenes* lipase (see e.g., EP 218 272), *P. cepacia* lipase (See e.g., EP 331 376), *P. stutzeri* lipase (See e.g., GB 1,372,034), *P. fluorescens* lipase, *Bacillus* lipase (e.g., *B. subtilis* lipase (Dartois et al. (1993) *Biochem. Biophys. Acta* 1131:253-260); *B. stearothermophilus* lipase (see e.g., JP 64/744992); and *B. pumilus* lipase (see e.g., WO 91/16422)).

Additional lipases include *Penicillium camembertii* lipase (Yamaguchi et al. (1991) *Gene* 103:61-67), Geotricum *candidum* lipase (See, Schimada et al. (1989) *J. Biochem.* 106:383-388), and various *Rhizopus* lipases such as *R. delemar* lipase (Hass et al. (1991) *Gene* 109:117-113), a *R. niveus* lipase (Kugimiya et al. (1992) *Biosci. Biotech. Biochem.* 56:716-719) and *R. oryzae* lipase. Additional lipases are the cutinase derived from *Pseudomonas mendocina* (See, WO 88/09367), and the cutinase derived from *Fusarium solani pisi* (WO 90/09446). Various lipases are described in WO 11/111143, WO 10/065455, WO 11/084412, WO 10/107560, WO 11/084417, WO 11/084599, WO 11/150157, and WO 13/033318. In some embodiments the lipase is one or more of M1 LIPASE™, LUMA FAST™, and LIPOMAX™ (DuPont Industrial Biosciences); LIPEX®, LIPOLASE® and LIPOLASE® ULTRA (Novozymes); and LIPASE P™ "Amano" (Amano Pharmaceutical Co. Ltd., Japan).

Amylases include, but are not limited to those of bacterial or fungal origin, or even mammalian origin. Numerous suitable are described in WO9510603, WO9526397, WO9623874, WO9623873, WO9741213, WO9919467, WO0060060, WO0029560, WO9923211, WO9946399, WO0060058, WO0060059, WO9942567, WO0114532, WO02092797, WO0166712, WO0188107, WO0196537, WO0210355, WO9402597, WO0231124, WO9943793, WO9943794, WO2004113551, WO2005001064, WO2005003311, WO0164852, WO2006063594, WO2006066594, WO2006066596, WO2006012899, WO2008092919, WO2008000825, WO2005018336, WO2005066338, WO2009140504, WO2005019443, WO2010091221, WO2010088447, WO0134784, WO2006012902, WO2006031554, WO2006136161, WO2008101894, WO2010059413, WO2011098531, WO2011080352, WO2011080353, WO2011080354, WO2011082425, WO2011082429, WO2011076123, WO2011087836, WO2011076897, WO94183314, WO9535382, WO9909183, WO9826078, WO9902702, WO9743424, WO9929876, WO9100353, WO9605295, WO9630481, WO9710342, WO2008088493, WO2009149419, WO2009061381, WO2009100102, WO2010104675, WO2010117511, WO2010115021, WO2013184577, WO9418314, WO2008112459, WO2013063460, WO10115028, WO2009061380, WO2009100102, WO2014099523, WO2015077126A1, WO2013184577, WO2014164777, PCT/US12/70334, PCT/US13/74282, PCT/CN2013/077294, PCT/CN2013/077134, PCT/CN2013/077137, PCT/CN2013/077142, PCT/CN2012/087135, PCT/US12/62209, PCT/CN2013/084808, PCT/CN2013/084809, and PCT/US14/23458. Commercially available amylases include, but are not limited to one or more of DURAMYL®, TERMAMYL®, FUNGAMYL®, STAINZYME®, STAINZYME PLUS®, STAINZYME ULTRA®, and BAN™ (Novozymes), as well as POWERASE™, RAPIDASE® and MAXAMYL® P, PREFERENZ® S100, PREFERENZ® S110, and PREFERENZ® S1000 (DuPont Industrial Biosciences).

Cellulases include but are not limited to those having color care benefits (see e.g., EP 0 495 257). Examples include *Humicola insolens* cellulases (See e.g., U.S. Pat. No. 4,435,307) and commercially available cellulases such as CELLUZYME®, CAREZYME® (Novozymes), and KAC-500(B)™ (Kao Corporation), and PRIMAFAST® GOLD (DuPont). In some embodiments, cellulases are incorporated as portions or fragments of mature wild-type or variant cellulases, wherein a portion of the N-terminus is deleted (See e.g., U.S. Pat. No. 5,874,276). Additional suitable cellulases include those found in WO2005054475, WO2005056787, U.S. Pat. Nos. 7,449,318, and 7,833,773.

Mannanases are described in U.S. Pat. Nos. 6,566,114, 6,602,842, 5, 476, and 775, 6,440,991, and U.S. Patent Application No. 61/739,267, all of which are incorporated herein by reference). Commercially available include, but are not limited to MANNASTAR®, PURABRITE™, and MANNAWAY®.

In some embodiments, peroxidases are used in combination with hydrogen peroxide or a source thereof (e.g., a percarbonate, perborate or persulfate) in the compositions of the present teachings, to the extent possible. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments.

Perhydrolases include the enzyme from *Mycobacterium smegmatis*. This enzyme, its enzymatic properties, its structure, and numerous variants and homologs, thereof, are described in detail in International Patent Application Publications WO 05/056782A and WO 08/063400A, and U.S. Patent Publications US2008145353 and US2007167344, which are incorporated by reference. In some embodiments, the *Mycobacterium smegmatis* perhydrolase, or homolog, includes the S54V substitution.

Other perhydrolases include members of the carbohydrate family esterase family 7 (CE-7 family) described in, e.g., WO2007/070609 and U.S. Patent Application Publication Nos. 2008/0176299, 2008/176783, and 2009/0005590. Members of the CE-7 family include cephalosporin C deacetylases (CAHs; E.C. 3.1.1.41) and acetyl xylan esterases (AXEs; E.C. 3.1.1.72). Members of the CE-7 esterase family share a conserved signature motif (Vincent et al., J. Mol. Biol., 330:593-606 (2003)).

Other perhydrolase enzymes include those from *Sinorhizobium meliloti, Mesorhizobium loti, Moraxella bovis, Agrobacterium tumefaciens*, or *Prosthecobacter dejongeii* (WO2005056782), *Pseudomonas mendocina* (U.S. Pat. No. 5,389,536), or *Pseudomonas putida* (U.S. Pat. Nos. 5,030,240 and 5,108,457).

IV. Hot-Melt Methods for Preparing Particles

Hot-melt particles can be prepared in a number of ways, for example hot-melt spinning disc atomization (also referred to as rotary disc cup atomization), hot-melt extrusion, and spray cooling (also referred to as spray chilling, spray congealing, and prilling) at elevated temperatures. (See, e.g., Kiran L. Kadam, ed., Granulation Technology for Bioproducts, Boca Raton, CRC Press, 1991). The granules may further be coated using, e.g., fluid bed coating.

V. Uses of the Present Hot-Melt Granules and Methods of Making, Thereof

The present compositions and methods offer commercially viable approaches for stabilization of enzymes in hot-melt granulation processes wherein the enzyme particulates are blended into a molten composition at temperatures as high as 150° C., or even as high as 180° C. Applications of the resulting hot-melt particles are numerous and include use in detergent compositions, animal feed, food, personal care and agricultural compositions.

EXAMPLES

Example 1: Stabilization of Phytase in Hot-Melt Spinning Disc Atomization Via Reduction of the Water Activity of Enzyme Powder Ingredient by Pre-Drying the Powder The main goal of this experiment was to investigate the effect of phytase powder water activity, which is a measure of free or unbound water in equilibrium with the total residual water, on the heat stability of enzyme in granulation with hot-melt spinning disc atomization. The initial water activity ($a_w$) of spray dried phytase powder was 0.147.

Enzyme granules were produced by the method of hot-melt spinning disc atomization using a 10-cm spinning disc in a rectangular chamber. The disc was installed at a height of 4.6 m from the collection surface. The granulation process involved mixing spray dried enzyme (i.e., phytase BP17; WO 2008/097619) powder into a homogenized molten preparation of polyethylene wax containing calcium carbonate at 152° C.; and dispensing the molten enzyme preparation onto the disc while spinning at 6,000 rpm. The length of enzyme processing time from the point of addition to the molten preparation until complete dispensing onto the disc was less 2 minutes. Atomized melt droplets solidified into granules as they projected away from the disc at room temperature and were collected for analysis. Prior to mixing, the $a_w$ of the original enzyme powder (Formulation B) was adjusted by either heat-drying under vacuum (Formulation A), moisturizing in a humidity chamber (Formulations C and D) to final $a_w$ values of 0.068, 0.147 (original value), 0.215 or 0.42. The final mixtures contained 20% (w/w) enzyme, 60% (w/w) non-polar, low viscosity metallocene-catalyzed polyethylene wax (LICOCENE® PE 4201; Clariant Corp.), 20% (w/w) low viscosity, high-melting point metallocene-catalyzed polyethylene wax (LICOCENE® PE 5301; Clariant Corp.), and 20% (w/w) calcium carbonate (GLC-1012; Great Lakes Calcium) in 400 g batch sizes.

The enzyme activity of the resulting enzyme granules, sieved to select for the 212-300 um size range, was measured using the Malachite-Green assay for measuring inorganic phosphate (see, e.g., Hwang et al. (2015) Delivery of Formulated Industrial Enzymes with Acoustic Technology, Journal of Laboratory *J Lab Automation,* 1-13). The granulation activity yield, i.e., the ratio of the 'measured' enzyme activity to the 'expected' enzyme activity, of phytase in the granules is shown in Table 1, below. The $a_w$ of phytase powder was ad

TABLE 1

Granulation activity yield of phytase granules

| Formulation | $a_w$ of phytase powder | $a_w$ of phytase granules | Granulation activity yield (%) |
|---|---|---|---|
| A | 0.068 | 0.118 | 81.4% |
| B | 0.147 | 0.207 | 73.1% |
| C | 0.215 | 0.267 | 71.7% |
| D | 0.420 | 0.418 | 53.5% |

The granulation activity yield increased with decreased $a_w$ of the enzyme powder ingredient. The $a_w$ of enzyme granules correlated well with the $a_w$ of enzyme powder ingredient. The results of this experiment suggest that reducing the water activity of the enzyme powder ingredient can be a viable approach to stabilize the enzyme in hot-melt spinning disc atomization at operating temperatures as high as 152° C.

FIG. 1 shows the correlation between $a_w$ and residual moisture content (loss-on-drying method) values of phytase granules. Low $a_w$ (<0.3) and moisture content (<5%, loss-on-drying at 105° C.) are preferred for animal feed pelleting applications.

Example 2: Stabilization of Phytase in Hot-Melt Spinning Disc Atomization Via Reduction of the Water Activity of Active Enzyme Ingredient by Pre-Drying and Pre-Blending with a Desiccant The main objective of this experiment was to investigate pre-blending of enzyme powder with different aluminosilicate based compounds, including zeolites and diatomaceous earth, as a preferred method for reducing the water activity of enzyme composition to improve the enzyme activity yield in granulation with hot-melt spinning disc atomization. The chemical formula of the zeolites employed in this experiment, are listed in Table 2.

TABLE 2

Chemical formula of zeolites tested in the experiment of Example 2

| Name | Chemical Formula | Supplier |
|---|---|---|
| Zeolite (product number 96096) | $0.6K_2O.4Na_2O.Al_2O_3.2SiO_2.xH_2O$ | Sigma-Aldrich |
| ZEOMAX ® | $(Ca, Mg, Na_2, K_2)O.Al_2O_3.10SiO2.8H_2O$ | ZeoTech Corp. |
| KMI Zeolite | $3Na_2O.3Al_2O_3.30SiO_2.24H_2O$ | KMI Zeolite Inc. |

Enzyme granules were produced with hot-melt spinning disc atomization as described in Example 1. The water activity ($a_w$) of phytase powder was 0.078-0.092 prior to blending with an aluminosilicate type desiccant. The enzyme powder blend was then mixed into a homogenized molten preparation of zinc stearate containing 10% calcium carbonate (20% in the case of Formulation E) at 150-152° C. and dispensed onto the disc while spinning at 5,800-6,200 rpm. All mixtures contained 20% (w/w) enzyme and 60% (w/w) zinc stearate COAD® 33 (Norac). The variable components present in the remaining 20% (w/w) of the mixtures are shown in Table 3, below.

TABLE 3

Composition of enzyme granules produced with hot-melt spinning disc atomization

| Formulation | Desiccant | Target wt % | Additive | Target wt % |
|---|---|---|---|---|
| E | — | — | — | — |
| F | Sigma-Aldrich Zeolite (P/N 96096) | 10% | — | — |
| G | Zeotech Corp. ZEOMAX ® < 90 um | 10% | — | — |
| H | KMI Zeolite Inc. KMI Zeolite < 90 um | 10% | — | — |
| I | EP Minerals CELATOM ® MN-2 | 10% | — | — |

TABLE 3-continued

| Composition of enzyme granules produced with hot-melt spinning disc atomization | | | | |
|---|---|---|---|---|
| Formulation | Desiccant | Target wt % | Additive | Target wt % |
| J | EP Minerals CELATOM ® MN-2 | 5% | EP Minerals PRE-CO-FLOC ® PB-300M | 5% |
| K | Sigma-Aldrich Zeolite (P/N 96096) | 5% | EP Minerals PRE-CO-FLOC ® PB-300M | 5% |
| L | Sigma-Aldrich Zeolite (P/N 96096) | 5% | EP Minerals PRE-CO-FLOC ® PB-200M | 5% |

The enzyme activity of the resulting enzyme granules (212-300 um size range) was measured as in Example 1 with Malachite-Green assay and the granulation activity yield is shown in Table 3.

TABLE 3

| Granulation activity yield of enzyme granules produced with hot-melt spinning disca tomization | | | |
|---|---|---|---|
| Formulation | $a_w$ phytase powder* | $a_w$ phytase granules | Granulation activity yield (%) |
| E | 0.086 | 0.150 | 84.1% |
| F | 0.078 | 0.001 | 90.4% |
| G | 0.078 | 0.239 | 95.5% |
| H | 0.078 | 0.203 | 88.8% |
| I | 0.078 | 0.241 | 84.9% |
| J | 0.092 | 0.239 | 88.3% |
| K | 0.092 | 0.106 | 89.5% |
| L | 0.092 | 0.062 | 90.8% |

*before blending with desiccant

Compositions containing Sigma-Aldrich Zeolite (Type 3A) showed higher granulation activity yield compared to those prepared with KMI Zeolite or CELATOM® MN-2 as desiccant. It is noteworthy that the $a_w$ of enzyme granules containing Sigma-Aldrich Zeolite (Type 3A) was considerably lower than other compositions. Our experiment with physical dry blends of phytase powder and Zeolite 3A powder showed a rapid drop of $a_w$ and moisture content of the phytase powder to respectively less than 0.005 and less than 0.3% upon blending two parts enzyme with 1-part zeolite. These $a_w$ and moisture values were maintained when the enzyme/zeolite (2:1 w/w) blend was kept in a closed container at normal room temperature for up to 7 days (duration of experiment). The results of the hot-melt granulation experiment suggested that reducing the water activity of enzyme powder ingredient by means of pre-blending the powder with an aluminosilicate desiccant can be a viable approach to stabilize the enzyme in hot-melt spinning disc atomization at operating temperatures as high as 152° C.

What is claimed is:

1. A hot-melt-prepared enzyme granule, comprising a mixture of a particulate enzyme powder and a desiccant having a water activity of less than 0.15, wherein the desiccant comprises a zeolite having a $SiO_2/Al_2O_3$ ratio of 20 or less, and wherein the desiccant releases less than 10% of bound water at a temperature above 50° C.

2. The granule of claim 1, wherein the desiccant releases less than 10% of bound water at a temperature less than 180° C.

3. The granule of claim 2, wherein the ratio of enzyme powder to desiccant is between 0.1:10 (w/w) to 10:0.1 (w/w).

4. The granule of claim 3, wherein the ratio of enzyme powder to desiccant is between 2:1 (w/w) to 4:1 (w/w).

5. The granule of claim 4, wherein the desiccant is a zeolite with low-silica having a $SiO_2/Al_2O_3$ ratio of less than 4.

6. The granule of claim 4, wherein the $SiO_2/Al_2O_3$ ratio is between 4 and 10.

7. The granule of claim 4, wherein the $SiO_2/Al_2O_3$ ratio is between 10 and 20.

8. The granule of claim 7, wherein the desiccant is a zeolite with pores smaller than 1.0 nm.

9. The granule of claim 8, wherein the desiccant is an activated zeolite, where the desiccant is dehydrated to at least 5% of its original water content.

10. The granule of claim 9, wherein the desiccant has a water absorption capacity of at least 20 g water per 100 g of desiccant at 50° C.

11. The granule of claim 10, further comprising a colored saturation indicator.

12. A detergent, animal feed, food, personal care or agricultural composition comprising the granule of claim 11.

13. The granule of claim 1, wherein the desiccant has a water activity of less than 0.10.

14. The granule of claim 13, wherein the desiccant has a water activity of less than 0.08.

15. The granule of claim 14, wherein the desiccant has a water activity of less than 0.05.

16. The granule of claim 15, wherein the desiccant has a water activity of less than 0.01.

17. The granule of claim 16, wherein the desiccant has a water activity of less than 0.005.

18. The granule of claim 3, wherein the ratio of enzyme powder to desiccant is between 0.1:5 (w/w) to 5:0.1 (w/w).

19. The granule of claim 18, wherein the ratio of enzyme powder to desiccant is between 0.1:1 (w/w) to 1:0.1 (w/w).

20. The granule of claim 7, wherein the desiccant is a zeolite with pores smaller than 0.75 nm.

21. The granule of claim 20, wherein the desiccant is a zeolite with pores smaller than 0.60 nm.

22. The granule of claim 21, wherein the desiccant is a zeolite with pores smaller than 0.40 nm.

23. The granule of claim 7, wherein the desiccant is an activated zeolite, where the desiccant is dehydrated to at least 50% of its original water content.

24. The granule of claim 7, wherein the desiccant is an activated zeolite, where the desiccant is dehydrated to at least 95% of its original water content.

* * * * *